(12) United States Patent
Harvey et al.

(10) Patent No.: US 6,309,454 B1
(45) Date of Patent: *Oct. 30, 2001

(54) FREEZE-DRIED COMPOSITE MATERIALS AND PROCESSES FOR THE PRODUCTION THEREOF

(75) Inventors: Wil Harvey, Skipton (GB); Peter Van Leeuwen, Hamburg (DE); Tom Hyland, Boatbridge; Will Aitken, Harrogate, both of (GB)

(73) Assignee: Johnson & Johnson Medical Limited, Edinburgh (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 30 days.

(21) Appl. No.: 09/570,105

(22) Filed: May 12, 2000

(51) Int. Cl.$^7$ .................................................. C08J 9/26

(52) U.S. Cl. .................. 106/122; 521/84.1; 424/28.02; 536/56; 536/57

(58) Field of Search .................. 106/122; 521/84.1; 424/78.02; 536/56, 57

(56) References Cited

U.S. PATENT DOCUMENTS

| | | | |
|---|---|---|---|
| 3,157,524 | * 11/1964 | Artandi | 106/122 |
| 3,598,622 | 8/1971 | Kearney et al. | |
| 3,628,974 | * 12/1971 | Battista | 424/73 |
| 3,632,350 | * 1/1972 | Battista | 424/59 |
| 3,649,347 | * 3/1972 | Battista | 106/124 |
| 3,658,733 | 4/1972 | Billy et al. | |
| 4,265,233 | 5/1981 | Sugitachi et al. | |
| 4,412,947 | 11/1983 | Cioca | |
| 4,474,949 | 10/1984 | Chatterjee et al. | |
| 4,655,980 | 4/1987 | Chu | |
| 4,784,989 | 11/1988 | Hook et al. | |
| 4,789,401 | 12/1988 | Ebinger et al. | |
| 4,919,681 | 4/1990 | Tyler et al. | |
| 4,947,840 | 8/1990 | Yannas et al. | |
| 5,024,841 | 6/1991 | Chu et al. | |
| 5,076,265 | 12/1991 | Wokalek | |
| 5,110,604 | 5/1992 | Chu et al. | |
| 5,124,197 | 6/1992 | Bernardin et al. | |
| 5,149,332 | 9/1992 | Walton et al. | |
| 5,277,915 | 1/1994 | Provonchee et al. | |
| 5,298,015 | 3/1994 | Komatsuzaki et al. | |
| 5,405,953 | 4/1995 | Banker et al. | |
| 5,562,645 | 10/1996 | Tanzer et al. | |
| 5,562,646 | 10/1996 | Goldman et al. | |
| 5,580,974 | 12/1996 | Banker et al. | |
| 5,599,335 | 2/1997 | Goldman et al. | |
| 5,607,695 | 3/1997 | Ek et al. | |
| 5,634,914 | 6/1997 | Wilkes et al. | |
| 5,660,854 | * 8/1997 | Haynes et al. | 424/422 |
| 5,667,501 | 9/1997 | Fowler et al. | |
| 5,669,894 | 9/1997 | Goldman et al. | |
| 5,677,284 | 10/1997 | Li | |
| 5,679,372 | 10/1997 | Shimuzu et al. | |
| 5,738,860 | 4/1998 | Schonfeldt et al. | |
| 5,763,579 | 6/1998 | Gagnieu et al. | |
| 5,766,631 | 6/1998 | Arnold | |
| 5,824,007 | 10/1998 | Faraz et al. | |
| 5,843,852 | 12/1998 | Dutkiewicz et al. | |
| 5,972,366 | * 10/1999 | Haynes et al. | 424/422 |
| 5,972,908 | 10/1999 | Motte et al. | |
| 5,985,434 | 11/1999 | Qin et al. | |
| 6,022,556 | 2/2000 | Hardy | |
| 6,133,170 | * 10/2000 | Suennaga et al. | 442/334 |

FOREIGN PATENT DOCUMENTS

| | | |
|---|---|---|
| 2 094 658 A | 10/1993 | (CA) . |
| 0269876 B1 | 2/1991 | (CS) . |
| 3409372 A | 9/1985 | (DE) . |
| 4407875 | 9/1995 | (DE) . |
| 0 040 596 | 11/1981 | (EP) . |
| 0042253 | 12/1981 | (EP) . |
| 0 049 469 | 4/1982 | (EP) . |
| 0059265 | 9/1982 | (EP) . |
| 0075751 | 4/1983 | (EP) . |
| 0080956 | 6/1983 | (EP) . |
| 0090997 | 10/1983 | (EP) . |
| 0099758 | 2/1984 | (EP) . |
| 0114351 | 8/1984 | (EP) . |
| 0114887 | 8/1984 | (EP) . |
| 0049469 | 4/1985 | (EP) . |

(List continued on next page.)

OTHER PUBLICATIONS

Abstract AN 112:22627, Electrochemical oxidation of low–molecular weight dextran, Jankiewicz, Barbara: Soloniewicz, Rajmund, Inst. Gen. Chem., Polit. Lodz., Lodz, Pol., Chem. Stosow. (1988), vol. Date 1988, 32 (2), 293–299.

Derwent AN 89–348621 [48] XP2045441 (Title only).

MEDLINE Abstract No. 82047152.

WPI Abstract Accession No. 85–237601/39.

WPI Abstract Accession No. 85–15591/26.

International Search Report for PCT/GB 97/01726, Date of the actual completion of the international search Oct. 22, 1997.

International Search Report for PCT/GB 97/01725, Date of the actual completion of the international search Nov. 3, 1997.

* cited by examiner

Primary Examiner—Morton Foelak
(74) Attorney, Agent, or Firm—T. J. Shatynski

(57) ABSTRACT

The invention provides a sterile freeze-dried sponge, wherein at least 80% by weight of the sponge consists of collagen and oxidized regenerated cellulose in the weight ratio 60:40 to 40:60, wherein the sponge has a dry tensile strength of more than 3N and/or a wet tensile strength of more than 1 N. Preferably, the collagen has a degree of denaturation less than 20% and the sponge is substantially free of chemical cross-links. The invention also provides methods for the manufacture of sponges according to the invention.

9 Claims, No Drawings

FOREIGN PATENT DOCUMENTS

| | | |
|---|---|---|
| 0140596 | 5/1985 | (EP) . |
| 0145970 | 6/1985 | (EP) . |
| 0068048 | 1/1986 | (EP) . |
| 0 177 064 | 4/1986 | (EP) . |
| 0182842 | 6/1986 | (EP) . |
| 0183136 | 6/1986 | (EP) . |
| 0091821 | 10/1986 | (EP) . |
| 0197090 | 10/1986 | (EP) . |
| 0200574 | 11/1986 | (EP) . |
| 0209726 | 1/1987 | (EP) . |
| 0216378 | 4/1987 | (EP) . |
| 0227955 | 7/1987 | (EP) . |
| 0 238 839 A | 9/1987 | (EP) . |
| 0 267 015 A | 5/1988 | (EP) . |
| 0 312 208 A | 4/1989 | (EP) . |
| 0314909 | 5/1989 | (EP) . |
| 0360180 | 3/1990 | (EP) . |
| 380546 | 8/1990 | (EP) . |
| 0403650 | 12/1990 | (EP) . |
| 0411124 | 2/1991 | (EP) . |
| 0428541 | 5/1991 | (EP) . |
| 0431479 | 6/1991 | (EP) . |
| 0468114 | 1/1992 | (EP) . |
| 0502172 | 9/1992 | (EP) . |
| 0514691 | 11/1992 | (EP) . |
| 0533809 | 3/1993 | (EP) . |
| 0 562 862 | 9/1993 | (EP) . |
| 0562864 | 9/1993 | (EP) . |
| 0568334 | 11/1993 | (EP) . |
| 0575273 | 12/1993 | (EP) . |
| 0612252 | 8/1994 | (EP) . |
| 0624402 | 11/1994 | (EP) . |
| 0633789 | 1/1995 | (EP) . |
| 0637452 | 2/1995 | (EP) . |
| 0666082 | 8/1995 | (EP) . |
| 0667167 | 8/1995 | (EP) . |
| 0668097 | 8/1995 | (EP) . |
| 0669937 | 9/1995 | (EP) . |
| 0705868 | 4/1996 | (EP) . |
| 0814310 | 6/1996 | (EP) . |
| 0743066 | 11/1996 | (EP) . |
| 0 526 756 | 5/1997 | (EP) . |
| 0781564 | 7/1997 | (EP) . |
| 0797965 | 10/1997 | (EP) . |
| 0804245 | 11/1997 | (EP) . |
| 0837091 | 4/1998 | (EP) . |
| 0 907 664 | 8/2000 | (EP) . |
| 2 257 909 A | 1/1993 | (GB) . |
| 2266239 | 10/1993 | (GB) . |
| 2272645 | 5/1994 | (GB) . |
| 2280372 | 2/1995 | (GB) . |
| 2280850 | 2/1995 | (GB) . |
| 2301362 | 12/1996 | (GB) . |
| 2 314 840 A | 1/1998 | (GB) . |
| 2 314 842 A | 1/1998 | (GB) . |
| 2314840 | 1/1998 | (GB) . |
| 2314842 | 1/1998 | (GB) . |
| 2329181 | 3/1999 | (GB) . |
| 60087225 A | 5/1985 | (JP) . |
| WO87/07153 | 12/1987 | (WO) . |
| WO88/06043 | 8/1988 | (WO) . |
| WO90/13320 | 11/1990 | (WO) . |
| WO 91/04019 A | 4/1991 | (WO) . |
| WO93/04691 | 3/1993 | (WO) . |
| WO93/10731 | 6/1993 | (WO) . |
| WO93/11803 | 6/1993 | (WO) . |
| WO93/16717 | 9/1993 | (WO) . |
| WO94/17837 | 8/1994 | (WO) . |
| WO95/05857 | 3/1995 | (WO) . |
| WO95/12371 | 5/1995 | (WO) . |
| WO 95/18635 A | 7/1995 | (WO) . |
| WO96/15818 | 5/1996 | (WO) . |
| WO96/16643 | 6/1996 | (WO) . |
| WO96/17595 | 6/1996 | (WO) . |
| WO96/40033 | 12/1996 | (WO) . |
| WO97/24090 | 7/1997 | (WO) . |
| WO97/34645 | 9/1997 | (WO) . |
| WO97/37694 | 10/1997 | (WO) . |
| WO97/46265 | 12/1997 | (WO) . |
| WO98/00180 | 1/1998 | (WO) . |
| WO98/00446 | 1/1998 | (WO) . |
| WO98/18780 | 3/1998 | (WO) . |
| WO98/09590 | 4/1998 | (WO) . |
| WO98/17165 | 4/1998 | (WO) . |
| WO98/28360 | 7/1998 | (WO) . |
| WO98/31403 | 7/1998 | (WO) . |
| WO98/33822 | 8/1998 | (WO) . |
| WO98/45335 | 10/1998 | (WO) . |
| WO99/01166 | 1/1999 | (WO) . |
| WO99/20318 | 4/1999 | (WO) . |
| WO99/64081 | 12/1999 | (WO) . |
| WO99/64655 | 12/1999 | (WO) . |

* cited by examiner

FREEZE-DRIED COMPOSITE MATERIALS AND PROCESSES FOR THE PRODUCTION THEREOF

FIELD

The present invention relates to freeze-dried pads comprising a major fraction of a mixture of collagen and oxidized regenerated cellulose (ORC), and to processes for the production of such pads.

BACKGROUND

WO98/00180 describes the use of freeze-dried sponges of collagen admixed with oxidized regenerated cellulose (ORC) for the treatment of chronic wounds. Such sponges must in practice meet stringent requirements of purity, sterility and non-antigenicity.

It has not hitherto been possible to provide sponges of collagen/ORC mixtures having high reproducibility and high tensile strength both when wet and when dry. In particular, collagen is prone to denaturation when it is sterilized by gamma-irradiation. Furthermore, collagen sponges tend to disintegrate rather rapidly in wound fluid, especially in the presence of collagenase enzymes. Whilst this problem can be diminished by chemical cross-linking of the collagen sponge using cross-linking agents such as glutaldehyde, the use of such cross-linking agents can give rise to problems of toxicity and antigenicity.

SUMMARY OF THE INVENTION

Accordingly, it is an object of the present invention to provide physiologically acceptable, sterile sponge pads based on collagen/ORC mixtures that exhibit high tensile strength.

It is a further object of the present invention to provide physiologically acceptable, sterile sponge pads based on collagen/ORC mixtures that have very high purity, sterility and low bioburden.

It is a further object of the present invention to provide physiologically acceptable, sterile sponge pads based on collagen/ORC mixtures that have high uniformity.

It is a further object of the present invention to provide physiologically acceptable, sterile sponge pads based on collagen/ORC mixtures that exhibit reduced resorption rates under simulated physiological conditions.

It is a further object of the present invention to provide physiologically acceptable, sterile sponge pads based on collagen/ORC mixtures that exhibit high mechanical strength and long resorption times without chemical cross-linking.

The present invention provides a sterile freeze-dried sponge, wherein at least 80% by weight of the sponge consists of a mixture of collagen and oxidized regenerated cellulose in the weight ratio 60:40 to 40:60, and wherein the sponge has a dry tensile strength as herein defined of more than 3N.

The freeze-dried sponge pad is sterile. Preferably, the sterility assurance level is better than $10^{-6}$. Preferably, the sponge has been sterilized by gamma-irradiation.

The sponge comprises at least 80% by weight of a mixture of collagen and ORC in the rate ratio 60:40 to 40:60. Preferably, the weight ratio contains a small excess of collagen, in a range 50:50 to 40:60 ORC:collagen. Preferably, the freeze-dried sponge consists essentially of collagen, ORC, water and up to 5% of one or more therapeutically active substances such as growth factors. Preferably, the freeze-dried sponge contains no more than 1% by weight of constituents other than collagen, ORC and water.

The collagen content is determined by hydrolysing the collagen into its constituent amino acids and analyzing for hydroxyproline as detailed below. The collagen content is calculated to be 7.19 times the hydroxyproline content. The ORC content is determined by hydrolyzing it to its constituent monosaccharides and analyzing for glucuronic acid as detailed further below.

Preferably, the freeze-dried sponge has a pH, measured as hereinafter described, of from 2.3 to 4.0, preferably from 2.5 to 3.0.

Preferably, the sterile freeze-dried sponges according to the present invention have a degree of collagen denaturation, measured as hereinafter described, of less than 15%, preferably less than 10%, and more preferably less than 5%. It is a particularly advantageous feature of the freeze-dried sponges according to the present invention that the collagen is stabilized against denaturation by the gamma-irradiation used in the sterilizing. The degree of denaturation of the collagen is determined by treatment with trypsin to dissolve the denatured collagen (trypsin does not dissolve native collagen), followed by filtration and quantitation of the hydroxyproline in the filtrate, as detailed further below.

The sterile freeze-dried sponges according to the present invention preferably have a dry tensile strength (maximum load measured as hereinafter described) greater than 3N, preferably greater than 4N. Preferably, the dry tensile load at 20% extension, measured as hereinafter described, is greater than 2.5N, preferably greater than 3.5N. Preferably, the dry extension at break, measured as hereinafter described, is from 15 to 30%, preferably from 20 to 25%.

The tensile strength characteristics of the sponges according to the present invention are further characterised by wet strength measurements on samples that have been soaked for 15 minutes in PBS prior to testing. The resulting wet strength maximum load is preferably greater than 1N, more preferably greater than 1.25N. The wet load at 20% extension is greater than 0.1N, preferably greater than 0.2N, most preferably 0.2–0.3N. The wet extension at break is preferably 75–100% more preferably 80–90%.

Preferably, the sterile freeze-dried sponges according to the present invention are not chemically cross-linked. They have may some dehydrothermal cross-linking as a result of the freeze-drying process, but preferably there is no chemical cross-linking by glutaldehyde or the like. This reduces the antigenicity and processing costs of the sponges. The present invention achieves satisfactory physical properties of the sponges and sufficiently long resorption times in vivo by very careful control of the composition and manufacturing conditions of the sponges. In particular, the sponges preferably contain ORC fibers, wherein a volume fraction of at least 80% of the fibers have lengths in the range of 20 $\mu$m to 100 $\mu$m. Such a size distribution can be achieved, for example, by milling an ORC cloth, followed sieving the milled powder to remove fibers outside the range. Preferably, the average (mean by volume) length of the ORC fibers is in the range 250 $\mu$m to 450 $\mu$m.

The selection of ORC fiber lengths in this range results in easy mixing of the ORC and collagen and highly homogeneous products. The ORC is more thoroughly complexed with the collagen, which results in enhanced therapeutic properties of the sponge. Furthermore, the ORC is more effective to reduce denaturation of the collagen by gammaradiation during sterilization. Surprisingly, these advantages can be achieved while maintaining the tensile strength of the sponge despite the small size of the ORC fibers.

The desired physicochemical properties of the freeze-dried sponges according to the present invention are further achieved by the use of collagen that has undergone sequential alkali and acid treatment steps to purify the collagen substantially without denaturing the collagen fibers. Preferably, the bioburden (TVC) of the freeze-dried sponge according to the present invention is less than 100 cfu/g, more preferably less than 10 cfu/g, and most preferably less than 1 cfu/g.

The sterile freeze-dried sponges according to the present invention have high and uniform porosity, and a high liquid absorption capacity. The measured absorption of the uncompressed pads in 0.9% saline is preferably greater than 12 g/100 cm$^2$, more preferably greater than 15 g/100 cm$^2$.

Preferably, the sterile freeze-dried sponge according to the present invetnion has a resorption time under simulated physiological conditions as described in more detail below of more than 48 hours.

The present invention further provides a method of manufacture of a freeze-dried sponge pad comprising the steps of:
  providing an acidified paste of purified collagen fibers, wherein the collagen is less than 10% denatured;
  providing oxidized regenerated cellulose fibers, wherein at least 80% of said fibers have lengths in the range of 20 μm to 1000 μm;
  combining said collagen and said ORC fibers in a homogeneous aqueous dispersion in a weight ratio of 60:40 to 40:60 collagen:ORC, said aqueous dispersion being acidified to a pH in the range of 2.8 to 3.2 and having a total solids concentration of 0.8 to 1.2% by weight;
  pouring said aqueous dispersion into trays to a depth greater than 1 cm;
  freezing the dispersion to a temperature less than –30° C., followed by a temperature programmed freeze drying and dehydrothermal cross-linking to a final moisture content of 5–15% by weight;
  splitting the freeze-dried dispersion to remove surface layers and leave one or more pads; and
  sterilizing the one or more pads by gamma-irradiation.

Preferably, the process according to the present invention is carried out substantially without the use of any chemical cross-linking agents.

Preferably, the step of providing collagen comprises the following steps:
  providing fresh and unswollen splits of bovine corium;
  treating the corium splits with a solution containing sodium hydroxide and hydrogen peroxide to swell and sterilize the corium; then
  treating the corium with a aqueous alkali solution at a pH greater than 12 and temperature less than 50° C. for a period of 10–14 days; then
  treating the corium with a aqueous acid solution at a pH of 0.8–1.2 and temperature less than 50° C. until the pH of the corium splits drops to less than 2.5; then
  washing the corium, and comminuting the corium with sufficient water to form a paste.

This treatment results in a collagen of exceptional purity and uniformity, without significant denaturing of the collagen. The collagen paste may be stored in the frozen state, but preferably the collagen is not freeze-dried intermediate the above steps and the step of combining the collagen with the ORC.

Preferably, the step of providing oxidized regenerated cellulose fibers comprising milling an oxidized regenerated cellulose cloth and screening the milled particles to remove particles having size less than 20 μm or greater than 1000 μm.

Preferably, the step of dispersing the collagen and the ORC comprises the steps of:
  adding an acid-swollen collagen/water paste to acidified water;
  adding oxidized regenerated cellulose fibers to the acidified water; and
  homogenizing the resulting mixture.

DETAILED DESCRIPTION

The dispersion is poured into trays to a depth of at least 10 mm, preferably at least 20 mm, and frozen into blocks in the trays before freeze drying. The freezing is preferably carried out by placing the trays containing the slurry onto pre-chilled shelves at –55° C. The trays are then loaded into a freeze-dryer, held at –50° C. for two hours, then at –40° C. before starting the freeze-drying cycle. This freezing method gives more uniformly distributed ice crystals, and hence more uniform products, than simply blast freezing the slurry in the trays.

Preferably, the step of freeze drying is carried out with dehydrothermal cross-linking using a temperature program in the range –40° C. to +30° C., to give blocks of freeze dried material. The blocks are split to remove surface layers, and to provide one or more pads. The settling of collagen and ORC fibers in trays results in a desired orientation of collagen and ORC fibers in the final pads. Furthermore, splitting the final pads from a larger block ensures that they have high homogeneity and surface uniformity.

Preferably, the step of sterilizing is carried out by gamma-irradiation at a dose of 18–29 KGy. It has been found that surprisingly little denaturation of the collagen takes place in the sterilizing step, which may be due to a stabilizing effect of the ORC.

In preferred embodiments of the process according to the present invention, the weight ratio of collagen to oxidized regenerated cellulose is from 50:50 to 55:45 and the pH of the aqueous dispersion is from 2.9 to 3.1.

A specific embodiment of the process and product according to the present invention will now be described further, by way of example.

EXAMPLE 1

A freeze-dried collagen/ORC sponge is prepared as follows.

First, the collagen component is prepared from bovine corium as follows. Bovine corium is split from cow hide, scraped and soaked in sodium hypochlorite solution (0.03% w/v) to inhibit microbial activity pending further processing.

The corium is then washed with water and treated with a solution containing sodium hydroxide (0.2% w/v) and hydrogen peroxide (0.02% w/v) to swell and sterilize the corium at ambient temperature.

The corium splits then undergo an alkali treatment step in a solution containing sodium hydroxide, calcium hydroxide and sodium bicarbonate (0.4% w/v, 0.6% w/v and 0.05% w.v, respectively) at pH greater than 12.2, ambient temperature, and for a time of 10–10 days, with tumbling, until an amide nitrogen level less than 0.24 mmol/g is reached.

The corium splits then undergo an acid treatment step with 1% hydrochloric acid at ambient temperature and pH 0.8–1.2. The treatment is continued with tumbling until the corium splits have absorbed sufficient acid to reach a pH less than 2.5. The splits are then washed with water until the pH value of corium splits reaches 3.0–3.4.

The corium splits are then comminuted with ice in a bowl chopper first with a coarse comminution and then with a fine comminution setting. The resulting paste, which is made up in a ratio of 650 g of the corium splits to 100 g of water, as ice, is frozen and stored before use in the next stage of the process. However, the collagen is not freeze-dried before admixture with the ORC in the next stage.

The ORC component of the freeze-dried pad is prepared as follows. A SURGICEL cloth (Johnson & Johnson Medical, Arlington) is milled using a rotary knife cutter through a screen-plate, maintaining the temperature below 60° C.

The milled ORC powder and the required weight (according to solids content) of frozen collagen paste are then added to a sufficient amount of water acidified with acetic acid to obtain a pH value of 3.0 and a total solids content of 1.0%. The mixture is homogenized through a Fryma MZ130D homogenizer, progressively diminishing the settings to form a homogeneous slurry. The pH of the slurry is maintained at 2.9–3.1. The slurry temperature is maintained below 20° C., and the solids content is maintained at 1%±0.07.

The resulting slurry is pumped to a degassing vessel. Vacuum is initiated for a minimum of 30 minutes, with intermittent stirring, to degas the slurry. The slurry is then pumped into freeze-drier trays to a depth of 25 mm. The trays are placed onto freezer shelves where the temperature has been preset to −40° C. The freeze-drier programme is then initiated to dry and dehydrothermally cross-link the collagen and ORC to form thick sponge pads.

On completion of the cycle, the vacuum is released, the freeze-dried blocks are removed, and are then split to remove the top and bottom surface layers, and to divide the remainder of the blocks into 3 mm thick pads. The step of splitting the freeze-dried blocks into pads is carried out with a Fecken Kirfel K1 slitter.

Finally, the pads are die-cut to the desired size and shape on a die-cutter, packaged, and sterilized with 18–29 KGy of cobalt 60 gamma-irradiation. Surprisingly, this irradiation does not cause significant denaturation of the collagen, which appears to be stabilized by the presence of ORC.

The resulting freeze-dried collagen ORC pads have a uniform, white, velvety appearance. The thickness of the pads is 3.2±0.17 mm (N=8 batches). The collagen content is 54%±3.8% (N=12 batches). The hydroxyproline content is 7.6±0.5% (N=12 batches). The carboxylate content is 10.98±0.81% (N=12 batches). The ash content is 0.16±0.1% (N=12 batches). The heavy metals (lead) content is less than 1 ppm. The pH is 2.78±0.15. The denaturation level is 4.87±1.54%. The endotoxin level is 33.5±0.9 cfu/g. The bioburden level is 0.2±0.3 cfu/g. The moisture content (loss on drying) is 12.0±12.8%.

Procedure 1

The collagen content of the materials according to the present invention is measured as follows:

Briefly, collagen is hydrolysed into constituent amino acids. The amount of the amino acid hydroxyproline is determined by oxidizing with chloramine-T and then coupling with 4-dimethylamino-benzaldehyde to produce a coloured product, the concentration of which is measured spectophotometrically at 550 nanometers.

Hydrolysis of the samples is carried out with 6 molar hydrochloric acid at 105° C. until digestion is completed, which takes at least 16 hours. The solution is then neutralized to pH 6 with 6 molar NaOH solution. The solution is then diluted.

Typically, for a 10 mg sample, the procedure uses 1 ml of 6 molar HCl, and the final volume for analysis on dilution is 500 ml.

A 1.0 ml sample of the test solution is treated with 1.0 ml of an oxidant solution prepared by dissolving 7 gm of chloramine-T in 600 ml of citrate buffer. The mixture is allowed to stand for 10 minutes, after which 1.0 ml of 20% perchloric acid is added, mixed and allowed to stand for 5 minutes at room temperature.

The mixture is then treated with 1.0 ml of a colour reagent prepared by dissolving 30 gm of 4-dimethylamino benzaldehyde in 45 ml of perchloric acid (60% w/v) followed by dilution in 250 ml of propane-2-ol. The mixture was treated in a water bath at 60° C. for 20 minutes, cooled for 5 minutes, followed by reading the optical density at 550 nanometers. The optical density is compared against values measured for control samples of pure collagen at various concentrations, pure hydroxyproline at various concentrations, and blank control samples to arrive at the hydroxyproline content.

The collagen content of the sample in weight percent is obtained by multiplying the measured hydroxyproline content in weight percent by 7.19.

Procedure 2

The amount of denatured collagen present in the materials according to the present invention is determined as follows.

Briefly, native collagen is protected by its triple-helical structure against proteolytic enzymes except for specific collagenases. If the helical structure is damaged, the resulting denatured collagen is susceptible to other proteases, such as trypsin, and is degraded to peptides. In this procedure, trypsin-resistant native collagen is separated from the degraded peptides by salt precipitation, and non-native collagen present in the filtrate is quantitated by hydroxyproline analysis.

A sample of the material according to the invention (100 mg) is weighed into a 50 ml conical flask. To the flask is added 10 ml of tris-HCl buffer solution containing 500 units trypsin. Blank experiments without the trypsin enzyme are also run. The mixtures are shaken at 4° C. for 5 hours. Then 2.5 ml of 25% NACl in 3 molar acetic acid are added to each container and mixed thoroughly. The containers are then placed in a refrigerator at 4° C. for a minimum of 16 hours. The chilled extract is filtered through Whatman 541 filter paper into 50 ml beaker, and the hydroxyproline content of the sample of the filtrate is measured by the method according to Procedure 1. Denatured collagen is calculated as 7.19×the measured hydroxyproline level, and the percentage of denatured collagen is calculated by comparison with the total collagen content measured by Procedure 1.

Procedure 3

The ORC content of materials according to the present invention is measured by a method similar to that described by Bitter and Muir in *Analytical Chemistry* vol. 4 (1962), pages 300–334.

Briefly, the material is hydrolysed to its individual constituents using sulphuric acid. Upon hydrolysis, the ORC breaks down to glucuronic acid (approximately 80%) and glucose (20%). The glucuronic acid residues then undergo a colour reaction with carbozole, the absorbance of which is measured against a series of ORC standards to give an estimation of the ORC content.

Samples of the material under test (10 mg) are placed in hydrolysate tubes. Deionised water (0.5 ml) and concentrated sulphuric acid (3 ml) are added, and the mixture is mixed on a vortex mixer for 15 minutes and checked for complete dissolution of the sample.

An aliquot (0.1 ml) of each sample hydrolysate is added to 2.9 ml of sodium tetraborate solution (0.025 molar in concentrated sulphuric acid) and mixed using vortex mixer. The sample tubes are placed in a boiling water bath for 10 minutes, and then cooled. Then 0.1 ml of carbozole solution (0.125% in ethanol) is added to each tube and mixed thoroughly with a vortex mixer, followed by placing the tubes in a boiling water bath for 15 minutes and cooling. The absorbance of the resulting solutions at 523 nanometers is then measured against a zero concentration ORC standard.

Procedure 4

The number of bacteria, fungi or yeast organisms present in the materials according to the present invention is measured as follows.

A 2 gm sample of the material is extracted with 100 ml of sterile one-quarter strength Ringer's solution, and an aliquot (5 ml) is passed to a sterile membrane filter (pore size 0.45 m) for sterile filtration. The filters are placed onto a nutrient medium in a Petri dish, and incubated under sterile conditions for 48 hours at 30° C. to allow the growth of germ colonies which can be counted with the naked eye or under a stereomicroscope if necessary. Appropriate control blanks are also run.

The level of microbiological contamination of the samples is expressed as the total viable count (TVC) in colony forming units per gram (cfu/g) in accordance with the following formula:

$$TVC = [(N \times 100)/(5 \times W)]$$

where N is the count of colonies, W is the weight of the sample in grams, 100 is the volume of the extractant solution in ml, and 5 is the volume of the aliquot (5 ml) that is filtered.

Procedure 5

The wet and dry tensile strengths of the material according to the invention are measured as follows. Samples are die cut from a 3 mm thickness pad of the material. The sample dimensions are 2.5×12 cm. The samples are loaded into an Instron tensile tester with jaw face dimensions 50×25 ml. The dry tensile strength is measured as the load at 20% elongation and the load at break. The extension at break is expressed as the percentage of the initial jaw separation. A minimum of 5 specimens was tested.

The wet tensile measurements are carried out in the same way on samples that have been soaked for 15 minutes in phosphate buffered saline (PBS).

Procedure 6

The pH of solid materials according to the present invention is measured by macerating 100 gm of the material in 100 ml of deionised water, and measuring the pH of the resulting slurry with a glass electrode.

Procedure 7

The resorption rate of the composite materials according to the invention is measured in a flow of simulated wound fluid as follows.

A circular pad of the material under test, of thickness 3 mm and diameter 6 cm is placed in a cylindrical recess and covered with a layer of liquid-impermeable backing material. Simulated wound fluid (3.45 mg/l collagenase in phosphate buffered saline) was pumped radially at a rate of 2.5 ml, 7.5 ml or 12 ml/24 hours from an opening below the centre of the disk under test to six openings disposed radially around the edges of the disk under test, below the disk under test, to simulate low, medium and high wound exudate flow rates. The time to resorption was estimated as the time required for complete dissolution of the pad under test. This time was at least two days for the high flow rate, at least three days for the medium flow rate, and at least six days for the low flow rate.

Procedure 8

The liquid absorbency of the materials according to the present invention was measured as follows.

A sample (typically 2.5 cm×2.5 cm×0.3 cm) of the material under test was weighed dry, and then immersed in phosphate buffered saline (PBS) for 15 minutes, removed with tweezers, and weighed again. The liquid absorbency was then calculated in grams of absorbed liquid per gram (dry weight) of the material.

Procedure 9

The levels of bacterial endotoxin in the materials according to the present invention are determined as follows.

Briefly, endotoxins from gram-negative bacterial cell walls cause limulus amebocyte lysate (LAL) to gel. The test is conducted as a limit test, wherein the sample is determined to be positive or negative to the test, judged against pre-established endotoxin concentrations. Positive and negative controls are essential and are carried out with each test run. The control standard endotoxin has its potency verified against referenced standard endotoxin (USP EC6). Details of the method can be found in Carl Freudenberg Method 091,102 (pyrogenicity); in USP XXIII (1985); in the FDA Guidelines 1987 and in European Pharmacoepia 2.6.14 (1998).

The embodiment of Example 1 has been described by way of example only. Many other compositions and methods falling with the scope of the present invention will be apparent to the skilled reader.

What is claimed is:

1. A method of manufacture of a freeze-dried sponge pad comprising the steps of:
   providing an acidified paste of purified collagen fibers, wherein the collagen is less than 10% denatured;
   providing oxidized regenerated cellulose fibers, wherein at least 80% of said fibers have lengths in the range of 20 µm to 1000 µm;
   combining said collagen and said ORC fibers in a homogeneous aqueous dispersion in a weight ratio of 60:40 to 40:60 collagen:ORC, said aqueous dispersion being acidified to a pH in the range of 2.8 to 3.2 and having a total solids concentration of 0.8 to 1.2% by weight;
   pouring said aqueous dispersion into trays to a depth greater than 1 cm;
   freezing the dispersion to a temperature below −30° C., followed by a temperature programmed freeze drying and dehydrothermal cross-linking to a final moisture content of 5–15% by weight;
   splitting the freeze-dried dispersion to remove surface layers and leave one or more pads; and
   sterilizing the one or more pads by gamma-irradiation.

2. A method according to claim 1 carried out substantially without the use of any chemical cross-linking agents.

3. A method according to claim 1, wherein the step of providing collagen comprises the following steps:
   providing fresh and unswollen splits of bovine corium;
   treating the splits with a hypochloride solution to inhibit microbial activity;
   treating the corium with a solution containing sodium hydroxide and hydrogen peroxide to swell and sterilize the corium; then treating the corium with a aqueous alkali solution at a pH greater than 12 and temperature less than 50° C. for a period of ten-fourteen days; then treating the corium with a aqueous acid solution at a pH of 0.8–1.2 and temperature less than 50° C.; then washing the corium, and comminuting the corium with sufficient water to form a paste.

4. A method according to claim 1, wherein the step of providing oxidized regenerated cellulose fibers comprising milling an oxidized regenerated cellulose cloth and screening the milled particles to remove particles having size less than 20 µm or greater than 1000 µm.

5. A method according to claim 1, wherein the step of dispersing the collagen and the ORC comprises the steps of:

adding an acid-swollen collagen/water paste to acidified water;

adding oxidized regenerated cellulose fibers to the acidified water; and homogenizing the resulting mixture.

6. A method according to claim 1, wherein the step of freezing is carried out by placing the trays containing the aqueous dispersion onto chilled shelves in a freezer followed by holding the trays at a temperature below −30° C. until the freezing is complete.

7. A method according to claim 1, wherein the step of freeze drying is carried out with dehydrothermal cross-linking.

8. A method according to claim 1, wherein the step of sterilizing is carried out by gamma-irradiation at a dose of 18–29 KGy.

9. A method according to claim 1, wherein the weight ratio of collagen to oxidized regenerated cellulose is from 50:50 to 55:45 and the pH of the aqueous dispersion is from 2.9 to 3.1.

* * * * *